(12) United States Patent
Haun et al.

(10) Patent No.: US 11,427,798 B2
(45) Date of Patent: Aug. 30, 2022

(54) MICROFLUIDIC TISSUE DISSOCIATION DEVICE AND METHOD

(71) Applicant: THE REGENTS OF THE UNIVERSITY OF CALIFORNIA, Oakland, CA (US)

(72) Inventors: Jered Haun, Irvine, CA (US); Janice De Jesus, San Diego, CA (US); Elliot En-Yu Hui, Irvine, CA (US); Jiang Li, Diamond Bar, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 267 days.

(21) Appl. No.: 16/868,474

(22) Filed: May 6, 2020

(65) Prior Publication Data

US 2020/0283723 A1 Sep. 10, 2020

Related U.S. Application Data

(60) Continuation of application No. 15/413,201, filed on Jan. 23, 2017, now Pat. No. 10,683,480, which is a
(Continued)

(51) Int. Cl.
*B01L 3/00* (2006.01)
*C12M 1/00* (2006.01)
(Continued)

(52) U.S. Cl.
CPC ....... *C12M 47/04* (2013.01); *B01L 3/502753* (2013.01); *C12M 21/08* (2013.01);
(Continued)

(58) Field of Classification Search
CPC ..... B01L 2300/0816; B01L 2300/0864; B01L 2300/0887; B01L 2400/0487;
(Continued)

(56) References Cited

U.S. PATENT DOCUMENTS 4,883,763 A 11/1989 Holen et al.
8,080,380 B2 12/2011 Chee
(Continued)

FOREIGN PATENT DOCUMENTS

AU 2013216683 B2 9/2007
CA 2609361 A1 11/2006
(Continued)

OTHER PUBLICATIONS

Kim, M. Y. et al., Microfabrication of High-Resolution Porous Membranes for Cell Culture, J Memb. Sci. 452, 460-469 (2014).
(Continued)

*Primary Examiner* — Dean Kwak
(74) *Attorney, Agent, or Firm* — Vista IP Law Group LLP

(57) ABSTRACT

A tissue dissociation device includes an inlet coupled to a first stage having a single channel having an upstream end and a downstream end; a plurality of serially arranged intermediate stages, wherein a first intermediate stage of the plurality is fluidically coupled to the downstream end of the first stage, and wherein each subsequent intermediate stage of the plurality has an increasing number of channels (with channels of smaller dimensions); and an outlet coupled to a last stage of the intermediate stages.

11 Claims, 13 Drawing Sheets

Related U.S. Application Data division of application No. 14/309,720, filed on Jun. 19, 2014, now Pat. No. 9,580,678.

(60) Provisional application No. 61/837,857, filed on Jun. 21, 2013.

(51) Int. Cl.
  *G01N 1/28* (2006.01)
  *C12M 1/40* (2006.01)
  *C12M 3/00* (2006.01)
  *C12M 1/33* (2006.01)

(52) U.S. Cl.
  CPC ............. *C12M 21/18* (2013.01); *G01N 1/286* (2013.01); *B01L 2300/0816* (2013.01); *B01L 2300/0864* (2013.01); *B01L 2300/0887* (2013.01); *B01L 2400/0487* (2013.01); *B01L 2400/086* (2013.01); *C12M 45/02* (2013.01)

(58) Field of Classification Search
  CPC ........ B01L 2400/086; B01L 3/502753; C12M 21/08; C12M 21/18; C12M 45/02; C12M 47/04
  USPC .......... 422/502–504; 436/174, 180; 435/379, 435/309.1
  See application file for complete search history.

(56) References Cited

U.S. PATENT DOCUMENTS

| | | |
|---|---|---|
| 2002/0142470 A1 | 10/2002 | Clarke et al. |
| 2004/0137607 A1 | 7/2004 | Tanaami et al. |
| 2005/0138567 A1 | 6/2005 | Smith et al. |
| 2006/0223178 A1 | 10/2006 | Barber |
| 2007/0025876 A1 | 2/2007 | Nishijima et al. |
| 2007/0025930 A1 | 2/2007 | Rico-Lattes et al. |
| 2007/0026416 A1 | 2/2007 | Fuchs |
| 2007/0026426 A1 | 2/2007 | Fuchs |
| 2007/0092876 A1 | 4/2007 | Xu |
| 2009/0014360 A1 | 1/2009 | Toner et al. |
| 2009/0098541 A1 | 4/2009 | Southern |
| 2009/0155877 A1 | 6/2009 | Illiescu |
| 2010/0081189 A1 | 4/2010 | Zantl et al. |
| 2010/0190265 A1 | 7/2010 | Dufva et al. |
| 2011/0085950 A1 | 4/2011 | Lee et al. |
| 2012/0100521 A1 | 4/2012 | Soper |
| 2013/0149724 A1 | 6/2013 | Chander |
| 2013/0295598 A1 | 11/2013 | Marx et al. |
| 2014/0057311 A1 | 2/2014 | Kamm et al. |
| 2014/0120537 A1 | 5/2014 | Chang |
| 2014/0248621 A1 | 9/2014 | Collins |
| 2014/0377866 A1 | 12/2014 | Haun et al. |
| 2015/0231244 A1 | 8/2015 | Chi et al. |
| 2015/0285785 A1 | 10/2015 | Hahn |
| 2015/0285786 A1 | 10/2015 | Hanh et al. |
| 2015/0377861 A1 | 12/2015 | Pant et al. |
| 2016/0047735 A1 | 2/2016 | Grisham et al. |
| 2017/0131187 A1 | 5/2017 | Haun et al. |
| 2018/0106805 A1 | 4/2018 | Allen |

FOREIGN PATENT DOCUMENTS

| | | |
|---|---|---|
| CA | 2327789 C | 9/2007 |
| CA | 2760574 A1 | 11/2010 |
| CA | 2799901 A1 | 11/2011 |
| CA | 2924883 A1 | 3/2015 |
| CA | 162188 S | 1/2016 |
| CA | 2963468 A1 | 4/2016 |
| CA | 2572113 C | 4/2017 |
| CA | 2609361 C | 11/2017 |
| CN | 101443023 A | 5/2009 |
| CN | 106434542 A | 1/2010 |
| CN | 201389496 Y | 1/2010 |
| CN | 102458302 A | 5/2012 |
| CN | 102002478 B | 1/2013 |
| CN | 102861105 A | 1/2013 |
| CN | 103038333 A | 4/2013 |
| CN | 104630139 A | 5/2015 |
| CN | 105934155 A | 9/2016 |
| CN | 106834121 A | 6/2017 |
| DK | 1778834 T3 | 11/2010 |
| DK | 1778833 T3 | 6/2011 |
| DK | 1885382 T3 | 6/2011 |
| DK | 1599575 T3 | 1/2012 |
| DK | 1778834 T5 | 1/2012 |
| DK | 1921133 T3 | 8/2015 |
| DK | 1638507 T3 | 6/2017 |
| DK | 1670315 T3 | 8/2017 |
| DK | 2571975 T3 | 10/2017 |
| DK | 3046417 T3 | 10/2017 |
| EP | 2145951 A1 | 1/2010 |
| EP | 2145952 A1 | 1/2010 |
| EP | 1778833 B1 | 3/2011 |
| EP | 1885382 B1 | 3/2011 |
| EP | 2332555 A3 | 6/2011 |
| EP | 2343360 A1 | 7/2011 |
| EP | 2305276 A3 | 9/2011 |
| EP | 2308963 A3 | 9/2011 |
| EP | 2371943 A1 | 10/2011 |
| EP | 1778834 B9 | 11/2011 |
| EP | 1599575 B9 | 3/2012 |
| EP | 2348103 A3 | 7/2012 |
| EP | 2571975 A2 | 3/2013 |
| EP | 1743021 B1 | 3/2014 |
| EP | 1778293 B1 | 4/2015 |
| EP | 1776126 B1 | 5/2015 |
| EP | 1921133 B1 | 5/2015 |
| EP | 2980206 A1 | 2/2016 |
| EP | 2617427 B1 | 8/2016 |
| EP | 3046417 A4 | 9/2016 |
| EP | 3106511 A1 | 12/2016 |
| EP | 2422622 B1 | 1/2017 |
| EP | 1638507 B1 | 3/2017 |
| EP | 1670315 B1 | 4/2017 |
| EP | 2571975 B1 | 7/2017 |
| EP | 3046417 B1 | 7/2017 |
| EP | 2574663 B1 | 8/2017 |
| EP | 2380970 B1 | 12/2017 |
| EP | 3106512 B1 | 3/2018 |
| EP | 3299451 A1 | 3/2018 |
| EP | 2465923 B1 | 4/2018 |
| ES | 2364957 T3 | 9/2011 |
| ES | 2364689 T3 | 2/2012 |
| ES | 2373551 T3 | 2/2012 |
| ES | 2545385 T3 | 9/2015 |
| ES | 2633604 T3 | 9/2017 |
| ES | 2641547 T3 | 11/2017 |
| ES | 2649387 T3 | 1/2018 |
| HK | 1078009 A1 | 6/2011 |
| HK | 1096424 A1 | 2/2013 |
| HK | 1165261 A1 | 8/2015 |
| HR | P20171471 T1 | 11/2017 |
| JP | 2008278821 A | 11/2008 |
| JP | 2008278822 A | 11/2008 |
| JP | 2009-75067 | 4/2009 |
| JP | 2009189280 A | 8/2009 |
| JP | 2009189281 A | 8/2009 |
| JP | 2009189282 A | 8/2009 |
| JP | 2009269930 A | 11/2009 |
| JP | 2010032444 A | 2/2010 |
| JP | 2010043876 A | 2/2010 |
| JP | 2010075066 A | 4/2010 |
| JP | 2010075114 A | 4/2010 |
| JP | 2010095531 A | 4/2010 |
| JP | 2010127620 A | 6/2010 |
| JP | 2010127708 A | 6/2010 |
| JP | 2010148450 A | 7/2010 |
| JP | 2010148451 A | 7/2010 |
| JP | 2011010615 A | 1/2011 |
| JP | 2011010616 A | 1/2011 |
| JP | 2012051923 A | 3/2012 |
| JP | 2012075439 A | 4/2012 |

(56) References Cited

FOREIGN PATENT DOCUMENTS

| | | |
|---|---|---|
| JP | 2012149088 A | 8/2012 |
| JP | 2014031389 A | 2/2014 |
| JP | 05960689 B2 | 8/2016 |
| JP | 2016136956 A | 8/2016 |
| JP | 06208787 B2 | 10/2017 |
| JP | 2018030815 A | 3/2018 |
| KR | 2005109941 A | 11/2005 |
| KR | 2006025180 A | 3/2006 |
| KR | 2006030861 A | 4/2006 |
| KR | 2007002058 A | 1/2007 |
| KR | 2007017974 A | 2/2007 |
| KR | 2007038538 A | 4/2007 |
| KR | 2007089254 A | 8/2007 |
| KR | 779812 B1 | 11/2007 |
| KR | 2008017389 A | 2/2008 |
| KR | 811995 B1 | 3/2008 |
| KR | 2008103611 A | 11/2008 |
| KR | 930139 B1 | 12/2009 |
| KR | 2010029272 A | 3/2010 |
| KR | 1083454 B1 | 11/2011 |
| KR | 2012003961 A | 1/2012 |
| KR | 2012020143 A | 3/2012 |
| KR | 1127305 B1 | 4/2012 |
| KR | 2012038534 A | 4/2012 |
| KR | 1145508 B1 | 5/2012 |
| KR | 1150666 B1 | 7/2012 |
| KR | 1197909 B1 | 11/2012 |
| KR | 2013038412 A | 4/2013 |
| KR | 1278437 B1 | 6/2013 |
| KR | 1310578 B1 | 9/2013 |
| KR | 1400544 B1 | 5/2014 |
| KR | 2016055827 A | 5/2016 |
| KR | 2017115296 A | 10/2017 |
| KR | 2017115377 A | 10/2017 |
| MX | 2011011402 A | 2/2012 |
| MX | 2016003127 A | 10/2016 |
| WO | WO2003024215 A1 | 3/2003 |
| WO | WO2003053346 A2 | 7/2003 |
| WO | WO2003053362 A2 | 7/2003 |
| WO | WO2005012480 A2 | 2/2005 |
| WO | WO2006014156 A1 | 2/2006 |
| WO | WO20060175980 A1 | 7/2006 |
| WO | WO2006069349 A9 | 9/2006 |
| WO | WO2006039129 A8 | 12/2006 |
| WO | WO2007061530 A1 | 5/2007 |
| WO | WO2007139551 A1 | 12/2007 |
| WO | WO2008060466 A3 | 8/2008 |
| WO | WO2008013863 A3 | 10/2008 |
| WO | WO2008140046 A1 | 11/2008 |
| WO | WO2006112941 B1 | 12/2008 |
| WO | WO2006127007 A3 | 4/2009 |
| WO | WO2009055610 A1 | 4/2009 |
| WO | WO2009076548 A1 | 6/2009 |
| WO | WO2008140044 A8 | 8/2009 |
| WO | WO2009101910 A1 | 8/2009 |
| WO | WO2010021993 A1 | 2/2010 |
| WO | WO2010035709 A1 | 4/2010 |
| WO | WO2010073808 A1 | 7/2010 |
| WO | WO2010124235 A1 | 10/2010 |
| WO | WO2010127310 A1 | 11/2010 |
| WO | WO2011145075 A2 | 11/2011 |
| WO | 2012/139209 | 10/2012 |
| WO | WO2013144883 A2 | 10/2013 |
| WO | WO2013144883 A3 | 11/2013 |
| WO | WO2014016750 A1 | 1/2014 |
| WO | WO2014064642 A1 | 5/2014 |
| WO | WO 2014/130391 | 8/2014 |
| WO | WO2015042182 A1 | 3/2015 |
| WO | WO 2015/127126 | 8/2015 |
| WO | WO2015120388 A1 | 8/2015 |
| WO | WO2015140737 A1 | 9/2015 |
| WO | WO2016007434 A1 | 1/2016 |
| WO | WO2016054592 A1 | 4/2016 |
| WO | WO2017100328 A1 | 6/2017 |
| WO | WO2017115289 A1 | 7/2017 |
| WO | WO2017125159 A1 | 7/2017 |
| WO | WO2017195156 A1 | 11/2017 |

OTHER PUBLICATIONS

MACS Miltenyi Biotec, gentleMACSTM Dissociator, The gentle way of automated tissue dissociation, gentlemacs com, (2010) (2pages).
Bianchi, Francesca et al., A New Nonenzymatic Method and Device to Obtain a Fat Tissue Derivative Highly Enriched in Pericyte-Like Elements by Mild Mechanical Forces Human Lipoaspirates, Cell Transplantation, vol. 22, pp. 2063-2077, 2013.
Conde-Green, Alexandra et al., Effects of Centrifugation on Cell Composition and Viability of Aspirated Adipose Tissue Processed for Transplantation, Aesthetic Surgery Journal 30(2) 249-255 (2010).
Conde-Green, Alexandra et al., Infulence of decantation, washing and centrifugation on adipocyte and mesenchymal stem cell content of aspirated adipose tissue: A comparative stury, Journal of Plastic, Reconstructive & Aesthetic Surgery (2010) 63, 1375-1381.
Heneidi, Saleh et al., Awakened by Cellular Stress: Isolation and Characterization of a Novel Population of Pluripotent Stem Cells Derived from Human Adipose Tissue, PLOS ONE, www.plosone.org, Jun. 2013, vol. 8, Issue 6, e64752.
Banyard, Derk A. et al., Phenotypic Analysis of Stromal Vascular Fraction after Mechanical Shear Reveals Stress-Induced Progenitor Populations, Pastic and Reconstructive Surger, Aug. 2016, vol. 138, No. 2, Shear Stress Progenitor Morphogenesis, www.PRSJournal.com, 237e-247e.
Tonnard, Patrick et al., Nanofat Grafting: Basic Research and Clinical Applications, Plastic and Reconstructive Surgery, Oct. 2013, vol. 132, No. 4, Nanofat Grafting, www.PRSJournal.com, 2013.
Adams, Andre A. et al., Highly Efficient Circulating Tumor Cell Isolation from Whole Blood and Label-Free Enumeration Using Polymer-Based Microfluidics with an Integrated Conductivity Sensor, J Am Chem Soc., Jul. 9, 2008; 130(27): 8633-8641. doi:10.1021/ja8015022.
Office Action dated Oct. 17, 2019 in U.S. Appl. No. 15/421,206, (57 pages).
Alharbi, Ziyad et al., Conventional vs. micro-fat harvesting: How fat harvesting technique affects tissue-engineering approaches using adipose tissue-derived stem/stromal cells, Journal of Plastic, Reconstructive & Aesthetic Surgery (2013) 66, 1271-1278.
Bassaneze, Vinicius et al., Shear Stress Induces Nitric Oxide-Mediated Vascular Endothelial Growth Factor Production in Human Adipose Tissue Mesenchymal Stem Cells, Stem Cells Development, vol. 19, Nov. 3, 2010, 371-378.
Topcu, Alpaslan et al., Increasing the Viability of Fat Grafts by Vascular Endothelial Growth Factor, Arch Facial Plast Surg, vol. 14 (No. 4), Jul./Aug. 2014, 270-276, www.archfacial.com.
Notice of Allowance and Issue Fee dated Mar. 17, 2020 in U.S. Appl. No. 15/421,206, (14pages).
Notice of Allowance and Issue Fee dated Feb. 7, 2020 in U.S. Appl. No. 15/413,201, (18 pages).
Restriction Requirement dated May 7, 2019 in U.S. Appl. No. 15/421,206, (9pages).
Amendment and Response dated Jul. 3, 2019 in U.S. Appl. No. 15/421,206, (5pages).
PCT International Preliminary Report on Patentability (Chapter I of the Patent Cooperation Treaty) for PCT/US2017/036429, Applicant: The Regents of the University of California, Form PCT/IB/326 and 373, dated Dec. 20, 2018 (14pages).
Notice of Preliminary Rejection (non-final) dated Mar. 21, 2019 for Korean Patent Application No. 10-2019-7000183, Applicant: The Regents of the University of California (19pages).
Office Action dated Feb. 8, 2019 in U.S. Appl. No. 16/101,254, (46pages).
Office Action dated Oct. 31, 2018 in U.S. Appl. No. 16/101,254, (32pages).
Amendment and Response dated Jan. 29, 2019 in U.S. Appl. No. 16/101,254, (19pages).

(56) References Cited

OTHER PUBLICATIONS

Final Office Action dated Feb. 8, 2019 in U.S. Appl. No. 16/101,254, (46pages).
Request for Continued Examination and Response dated Apr. 18, 2019 in U.S. Appl. No. 16/101,254, (19pages).

MICROFLUIDIC TISSUE DISSOCIATION DEVICE AND METHOD

RELATED APPLICATIONS

This Application is a continuation of U.S. patent application Ser. No. 15/413,201 filed on Jan. 23, 2017, now issued as U.S. Pat. No. 10,683,480, which is a divisional application of U.S. patent application Ser. No. 14/309,720, filed on Jun. 19, 2014, now U.S. Pat. No. 9,580,678, which itself claims priority to U.S. Provisional Patent Application No. 61/837,857 filed on Jun. 21, 2013, which are hereby incorporated by reference in its entirety. Priority is claimed pursuant to 35 U.S.C. §§ 119, 120 and any other applicable statute.

FIELD OF THE INVENTION

The field of the invention generally relates to devices that are designed to dissociate tumor tissue. Tumor tissue may be obtained, for example, by a needle biopsy of cells that are formed into a suspension of cells that can then be run through the device. The device may be used in laboratory of medical office settings and may incorporate downstream processes and analysis such as molecular analysis.

BACKGROUND

Cancer is the second leading cause of death in the Western World, but is rapidly rising worldwide and is expected to become the number one killer in a few years. Thus, there is tremendous need to improve our understanding and ability to treat this deadly disease. Nearly all cancer types form solid tumors, abnormal tissue masses that are highly complex and dynamic. Recent evidence has pointed to a model in which tumors can be viewed as an ecosystem consisting of a diverse array of cell types that work in concert to maintain homeostasis and drive further development. This intra-tumor cellular heterogeneity has been identified as a key factor underlying progression, metastasis, and the development of drug resistance. Cell types can include neoplastic subpopulations with distinct genotypes and phenotypes that are generated through clonal evolution, differentiation from rare stem-like precursors/cancer stem cells, or most likely a combination of the two mechanisms. Host cells of diverse origins, including non-tumor epithelium, stroma, and immune subtypes, can also assist the tumor in different capacities. Thus, analyzing tumor heterogeneity and identifying the presence of key cell types have become major focus areas in tumor biology and clinical diagnostics. Knowledge of different cell types can also drive patient-specific protocols for cancer treatment.

A major challenge for solid tumor analysis is the fact that specimens are three-dimensional tissue structures. This is particularly true to assessing cellular heterogeneity and identifying rare cell types such as cancer stem cells. Tissue-based analysis methods such as histology, immunohistochemistry, and fluorescence in-situ hybridization are clinical standards that provide morphological and sub-cellular detail, but are low throughput and detection signals are difficult to quantitate and multiplex. Techniques that involve sample destruction such as genome/transcriptome sequencing, microarrays, mass spectrometry, and Western blotting can provide large amounts of molecular information but retain no context with respect to the cellular components in the original sample. Due to these limitations, researchers and clinicians are increasingly employing cell-based analysis platforms such as flow cytometry because they offer high-throughput and multiplexed information about each cell within the sample. Cell sorting can also be used to isolate rare cell types such as cancer stem cells, metastatic precursors, and drug resistance clones for additional study. The disadvantage is that the tissue must first be broken down into single cells, which requires considerable expenditure of time and effort. Moreover, dissociation can potentially damage or otherwise bias samples. Thus, tissue dissociation remains a major barrier to the application of single cell techniques to solid tumor specimens.

Tumor tissue is currently dissociated into single cells using proteolytic enzymes that digest cellular adhesion molecules and/or the underlying extracellular matrix. The tumor tissue specimen is first minced with a scalpel into ~1-2 mm pieces. The enzyme or enzyme cocktail of choice is then applied. Trypsin is a broadly reactive protease that is highly efficient, requiring only short incubation times on the order of 15 minutes. Unfortunately, trypsin can also cleave cell surface proteins that may provide important diagnostic information or regulate cell function. For example, it has been shown that CD44, a commonly used cancer stem cell marker, is cleaved by trypsin resulting in significantly reduced expression. Collagenase is a milder alternative that digests collagen within the underlying extracellular matrix, leaving cells largely undisturbed. For this reason, collagenase has been employed for identifying and isolating cancer stem cells via CD44 or other biomarkers. However, collagenase requires long incubation times on the order of 1 to 2 hours that could negatively affect cell viability or molecular expression. Non-enzymatic options such as the calcium chelator ethylenediaminetetraacetic acid (EDTA) can also be employed, but EDTA is much less efficient and therefore used only to augment protease digestion. Following initial enzymatic or chemical treatment procedure, samples are subjected to fluid shear forces to mechanically liberate individual cells. This is typically achieved by vortexing and/or repeatedly pipetting the sample. These methods generate poorly defined shear flow environments that do not allow control over sample exposure, potentially resulting in variations across different batches or laboratories. The gentleMACS™ Dissociator (Miltenyl Biotec) is a commercial system that has been developed to standardize mechanical dissociation, but its use with tumor specimens is not common and performance is not well documented.

A final step that is used in many dissociation processes is to remove large aggregates that remain by filtering, which results in loss of sample. Taken together, tumor tissue dissociation involves multiple manual processing steps that are time-consuming and labor intensive, and there are numerous areas for which the resulting cell suspension can be improved. Notably, enzymatic digestion is either harsh or very long, large aggregates are lost to filtering, and there is no way to control whether the recovered sample contains single cells versus small clusters. Thus, new technology and methodology development is critically needed to meet all of the following goals: (1) improve dissociation efficiency so that the entire sample is recovered as single cells, (2) maximize overall cell quality in terms of viability and molecular biomarker expression, (3) decrease processing time from hours to minutes, and (4) automate the entire workflow to enable point-of-care operation and direct connection to additional downstream tasks.

SUMMARY

In one embodiment, a microfabricated fluidic device is disclosed for processing tumor tissue samples into single cells. The device employs fluidic-containing channel features ranging, generally, in size from millimeters down to hundreds of microns. The channels also contain optional constriction and expansion regions that generate fluidic jets of varying size scales and magnitudes to help break down tissue fragments and cell aggregates using hydrodynamic shear forces. The design will enable gradual disaggregation, thereby maximizing cell yield without causing extensive cell damage. Moreover, the flow-through format will enable rapid processing and is ideal for connecting to downstream fluidic operations.

The fluidic device utilizes multiple dissociation regions or stages where hydrodynamic forces within the channels are used to dissociate the sample with the goal of disrupting tissue but maintaining structural integrity of cells. Features include a gradual decrease in cross-section across multiple stages (e.g., five (5) stages) of impingement channels going from a size, in one embodiment, that is larger than a needle cannula (e.g., 2000 µm or in some instances 500 µm) down to a size that is larger than single epithelial cells (e.g., 125 µm). The fluidic channels may be laser cut in at least three separate 250 µm high sheets of plastic (PET), which were connected by vias and bonded by adhesive and pressure lamination. In other embodiments, additional layers beyond three (3) may be used.

In another embodiment, a tissue dissociation device includes an inlet coupled to a first stage comprising a single channel having cross-section of x; a second stage coupled to a downstream end of the first stage, the second stage comprising two channels having a cross-section of x/2; a third stage coupled to a downstream end of the second stage, the third stage comprising four channels having a cross-section of x/4; a fourth stage coupled to a downstream end of the third stage, the fourth stage comprising eight channels having a cross-section of x/8; a fifth stage coupled to a downstream end of the fourth stage, the fifth stage comprising sixteen channels having a cross-section of x/16; and an outlet coupled to the fifth stage.

In another embodiment, a tissue dissociation device includes an inlet coupled to a first stage comprising a single channel having an upstream end and a downstream end. The device has a plurality of serially arranged intermediate stages, wherein a first intermediate stage of the plurality is fluidically coupled to the downstream end of the first stage, and wherein each subsequent intermediate stage of the plurality has an increasing number of channels. The device has an outlet coupled to a last stage of the intermediate stages.

In another embodiment, a method of dissociating tumor tissue includes inserting a sample containing tissue into a tissue dissociation device comprising a plurality of serially arranged stages, wherein each subsequent stage of the plurality has an increasing number of channels and channels of decreasing dimensions; flowing the tissue through the plurality of serially arranged stages; and collecting a sample after flowing through the plurality of serially arranged stages.

DETAILED DESCRIPTION OF THE ILLUSTRATED EMBODIMENTS

Figure 1:
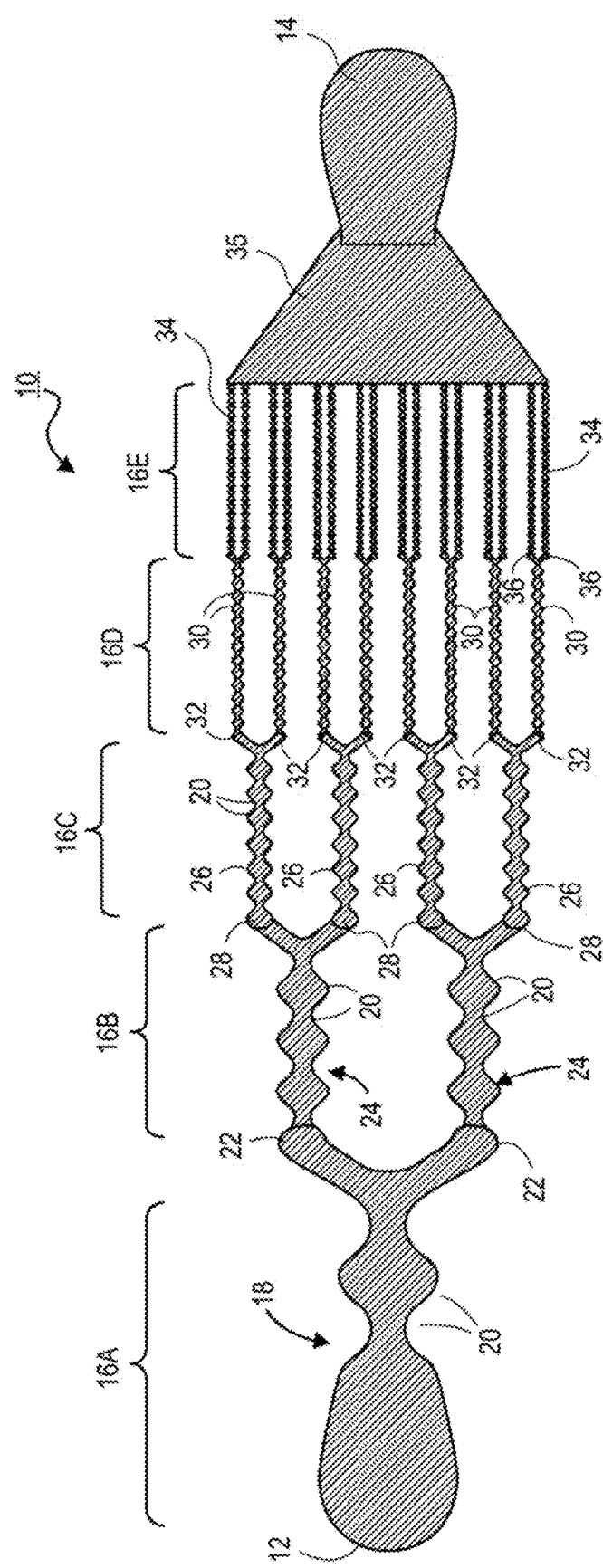
FIG. 1 illustrates a plan view of a tissue dissociation device according to one embodiment. The device includes five stages.

FIG. 1 illustrates a tissue dissociation device 10 according to one embodiment. The tissue dissociation device 10 is a fluidic-based device in which a fluid containing tissue samples therein (e.g., tumor tissue samples) is flowed through. The tissue dissociation device 10 is preferably made from multiple layers (see FIG. 3) which are laminated together to form the completed tissue dissociation device 10. For example, hard plastic such as polyethylene terephthalate (PET) can be laser cut into desired patterns and then aligned in a stack and fused together using intermediate adhesive layer(s) and pressure lamination. The hard plastic format is more robust than alternatives produced using photolithography and polydimethyl siloxane (PDMS). This is important because the tissue dissociation device may need to support high flow rates and pressures to effectively dissociate tissues. Still referring to FIG. 1, the device includes an inlet 12 and an outlet 14 as well as plurality of serially connected stages 16A, 16B, 16C, 16D, 16E formed within the tissue dissociation device 10 between the inlet 12 and the outlet 14. The first stage 16A of the tissue dissociation device 10 includes a single channel 18 this is connected at an upstream side to the inlet 12 and contains therein a plurality of expansion and constriction regions 20 therein. The expansion and constrictions regions 20 are formed within the channel 18 and are alternating regions where the width of the channel 18 increases and decreases. The expansion and constrictions regions 20 generate fluidic jets of varying size scales and magnitudes to help break down tissue fragments and cell aggregates using hydrodynamic shear forces. The design of the expansion and constrictions regions 20 will enable gradual disaggregation, thereby maximizing cell yield without causing extensive cell damage. Moreover, the flow-through format will enable rapid processing and is ideal for connecting to downstream fluidic operations.

In one embodiment, the expansion and constriction regions 20 are a continuous expansion and constriction of the channel width. This will modulate fluid velocity, actively mixing the sample and generating shear forces across cell aggregates. The expansion and constriction regions are connected by smooth curved lines, resulting in relatively gradual velocity changes to avoid that turbulent mixing and recirculating flows. In one embodiment, the maximum width in the expansion region is 3-fold greater than the minimum width in the constriction, and this ratio is maintained throughout the device 10. In this embodiment, the constriction regions are separated by a distance equal to the expansion region width. This results in an increase in the number of constrictions per channel through the device 10.

The second stage 16B is connected to the downstream end of the first stage 16A at the end of the channel 18. The second stage 16B may be located in a different layer of the tissue dissociation device 10 than the first stage 16A whereby the second stage 16B is connected to the first stage 16A using a vias 22. The second stage 16B includes a plurality of channels 24 with each channel 24 having a plurality of expansion and constriction regions 20 formed therein. In addition, the dimensions of the channels 24 within the second stage 16B are narrowed as compared to the channel 18 of the first stage 16A. In one aspect of the invention, the second stage 16B includes two channels 24 wherein the width of each channel 24 is reduced by a factor of x/2 where x represents the width of the channel 18 of the first stage 16A. The height of the channels 18, 24 remains the same (e.g., 300 µm).

Still referring to FIG. 1, a third stage 16C is connected to the end of the second stage 16B. The third stage 16C includes four channels 26 with pairs of channels 26 connecting to the downstream end of the channels 24. The interface between the end of the second stage 16B and the beginning of the third stage 16C may be accomplished through vias 28. In one aspect of the invention, the third stage 16C includes four channels 26 wherein the width of each channel 26 is reduced by a factor of x/4 where x represents the width of the channel 18 of the first stage 16A. The third stage 16C may be located in a different layer of the device 10 from the upstream second stage 16B.

A fourth stage 16D is connected to the end of the third stage 16C. The fourth stage 16D includes eight channels 30 with pairs of channels 30 connecting to the downstream end of the channels 26. The interface between the end of the third stage 16C and the beginning of the fourth stage 16D may be accomplished through vias 32. In one aspect of the invention, the fourth stage 16D includes eight channels 30 wherein the width of each channel 26 is reduced by a factor of x/8 where x represents the width of the channel 18 of the first stage 16A.

A fifth stage 16E is connected to the end of the fourth stage 16D. The fifth stage 16E includes sixteen channels 34 with pairs of channels 34 connecting to the downstream end of the channels 30. The interface between the end of the fourth stage 16D and the beginning of the fourth stage 16D may be accomplished through vias 36. In one aspect of the invention, the fifth stage 16E includes sixteen channels 34 wherein the width of each channel 26 is reduced by a factor of x/16 where x represents the width of the channel 18 of the first stage 16A. The output of the sixteen channels 34 are combined in a single downstream channel 35 that leads to the outlet 14.

Figure 2:
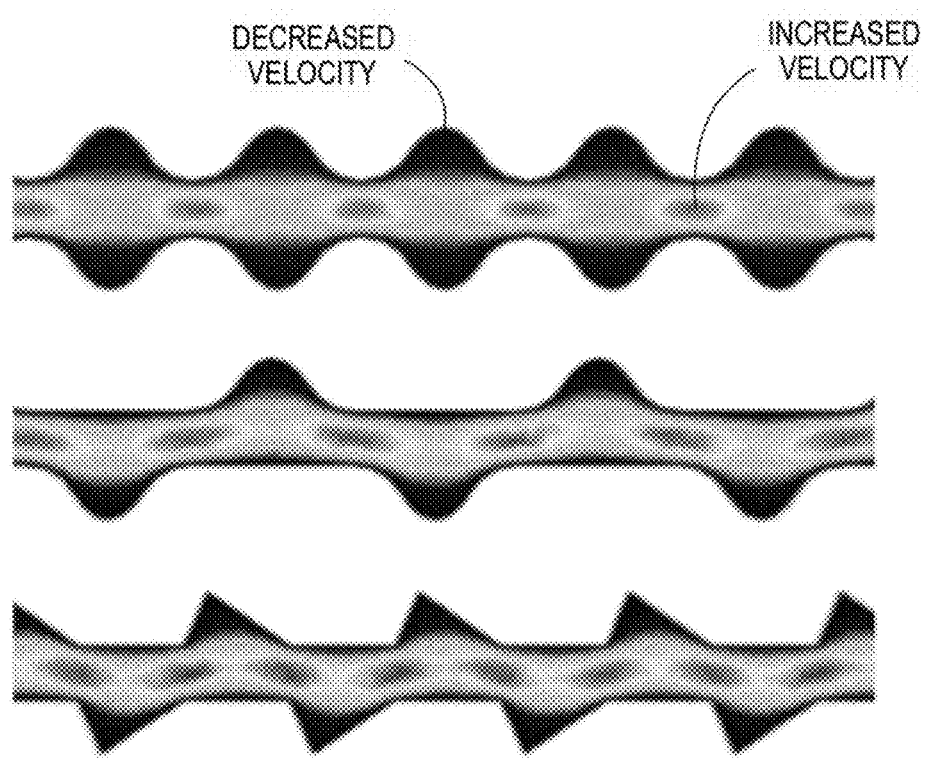
FIG. 2 illustrates alternative channel designs for use within the stages of the device. The channel designs include different-shaped expansion and constriction regions. Computer implemented fluid dynamic simulations within each channel are also illustrated. Areas of increased velocity are in the constriction regions while areas of decreased velocity are in the expansion regions.

Note that in the above embodiment, because the width of the channels 24, 26, 20, 34 decreases by half as channel number doubles, and channel height is constant, the average fluid velocity in each channel 18, 24, 26, 20, 34 is constant throughout the device 10. The vias 22, 28, 32, and 36 have diameters equal to the cross-section of the channels in the subsequent stage. The vias 22, 28, 32, and 36 act as a minimum size feature. Maintaining laminar flow is important so that flow properties remain well-defined. Velocity profiles of various expansion and constriction regions 20 are depicted in FIG. 2. These are slices across the channel width, with the other dimension viewed at the centerline. With respect to channel width, flow velocity increases in the constriction regions to form discrete jets of high fluid flow. A key aspect is that the maximum velocity within these fluidic jets increases with each stage. The jets thus increase in dissociation power as they become smaller in scale as one moves in the downstream direction. These regions act as hydrodynamic micro-scalpels that become sharper and finer throughout the device, progressively breaking down tissue into smaller aggregates and finally single cells. This is a consequence of holding average velocity constant at smaller dimensions, as the velocity profile must extend to higher values as it is compressed because of the no-slip condition at the wall.

Figure 3:
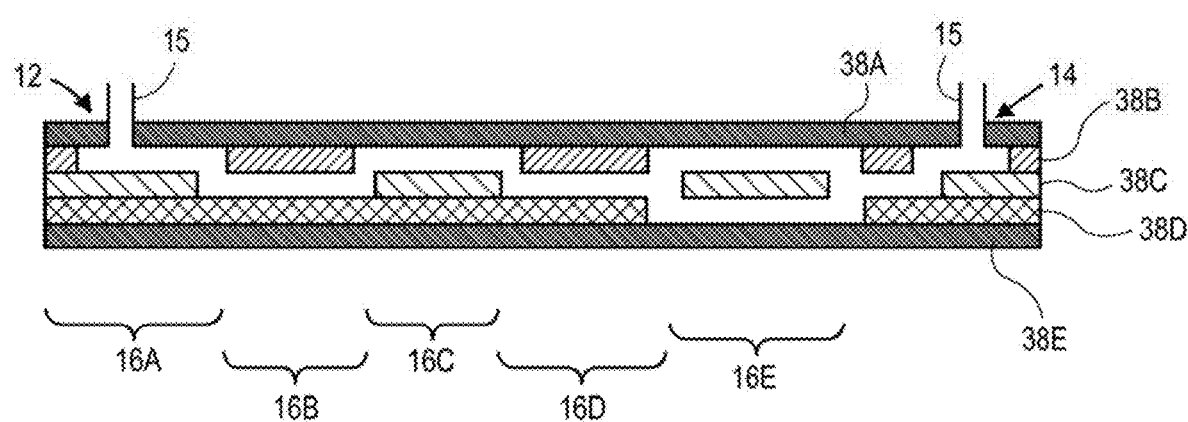
FIG. 3 illustrates a side, cross-sectional view of the tissue dissociation device of the embodiment of FIG. 1.
Figure 4:
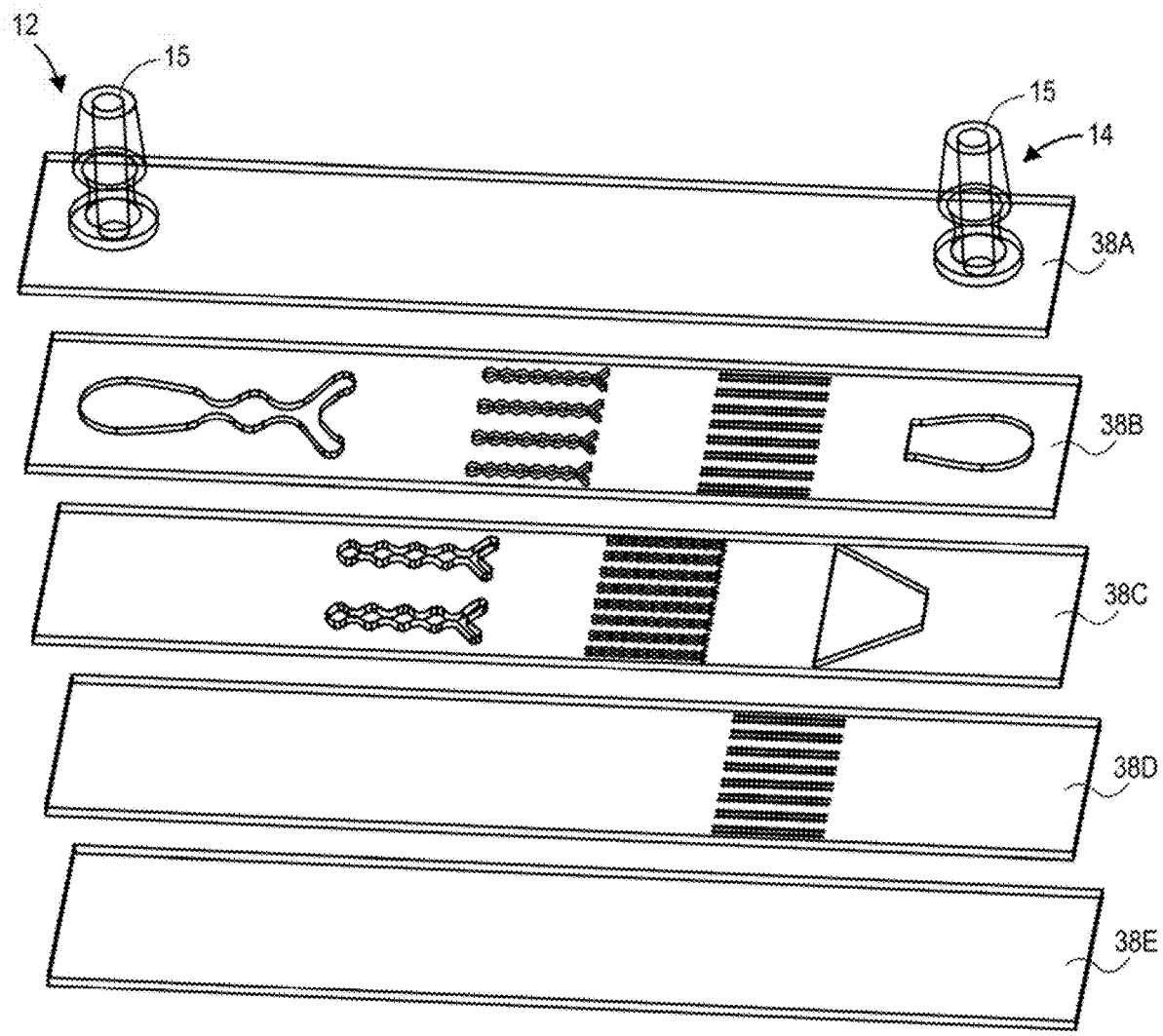
FIG. 4 illustrates an exploded view of the tissue dissociation device of FIG. 3.
Figure 5:
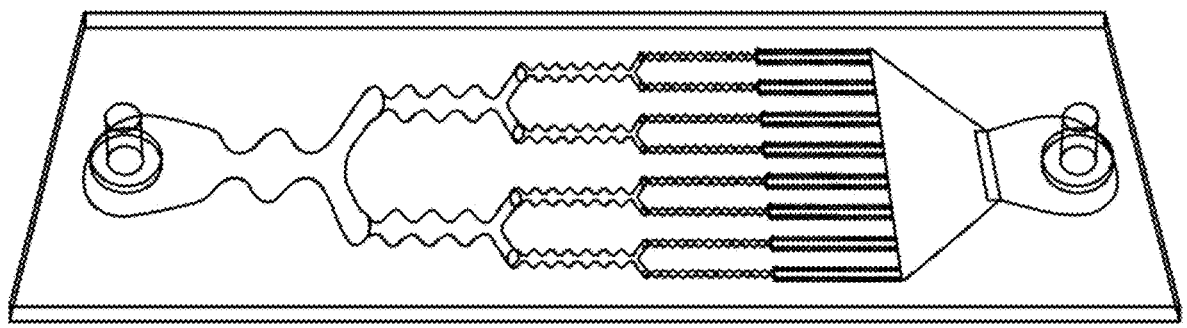
FIG. 5 illustrates a perspective view of a tissue dissociation device according to one embodiment.

As noted herein, the tissue dissociation device 10 may be formed in different layers of a multi-layered laminate structure. For example, FIG. 3 illustrates a side view of a tissue dissociation device 10 that includes five total layers 38A, 38B, 38C, 38D, 38E with various stages 16A-16E located within these layers. Placing different stages 16A-16E in different layers adds structural integrity of the tissue dissociation device 10 enabling the same to operate at high flow rates and pressures. For example, in the embodiment of FIG. 3, the first stage 16A is located in layer 38B while stages 16B and 16D are located in layer 38C. The fifth stage 16E is located in layers 38B and 38D. Layer 38A is the top of the tissue dissociation device 10 and includes barbs 15 or the like that provide connections tubing or other conduit that can be connected to both the inlet 12 and the outlet 14. In one embodiment, the height of the channels 18, 24, 26, 30, 34 are approximately 300 μm which includes 250 μm of PET plastic forming the layers and 50 μm of adhesive between adjacent layers (not shown). FIG. 4 illustrates an exploded, perspective view of the device of FIG. 3 showing the various layers 38A-38E that are laminated together to make the final tissue dissociation device 10. FIG. 5 illustrates a perspective view of the completed tissue dissociation device 10.

Figure 6:
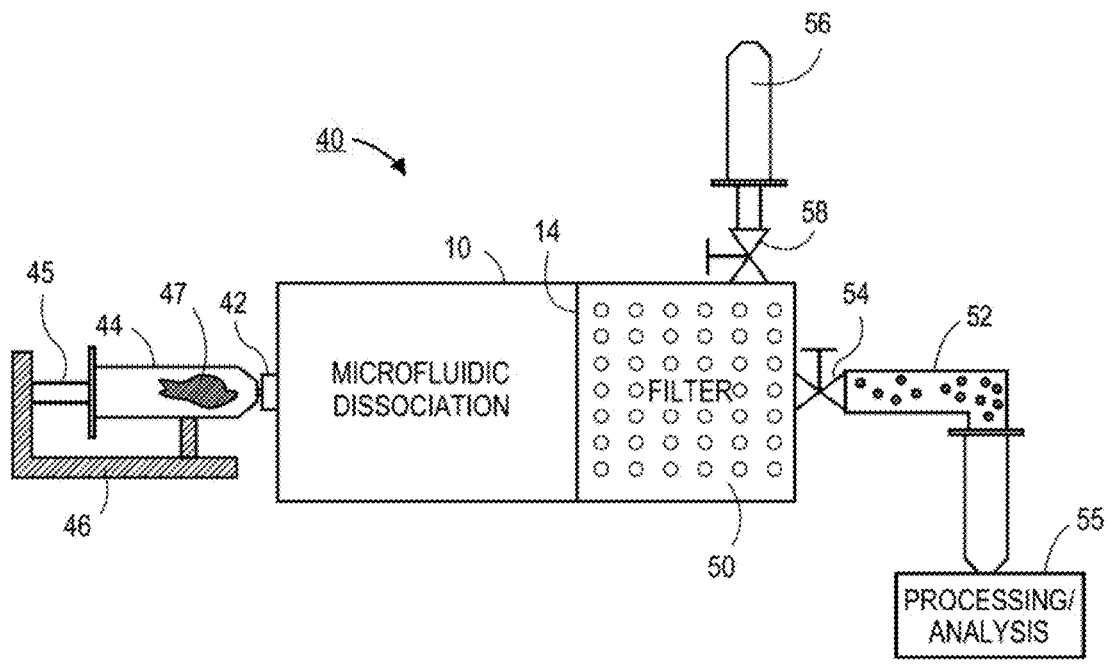
FIG. 6 illustrates a system integrating the tissue dissociation device according to one embodiment.
Figure 7:
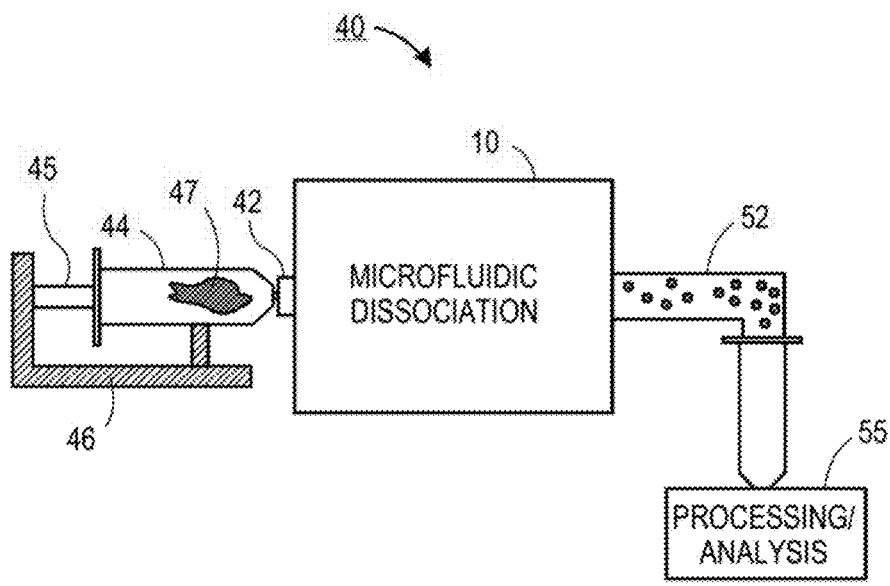
FIG. 7 illustrates a system integrating the tissue dissociation device according to another embodiment.
Figure 8:
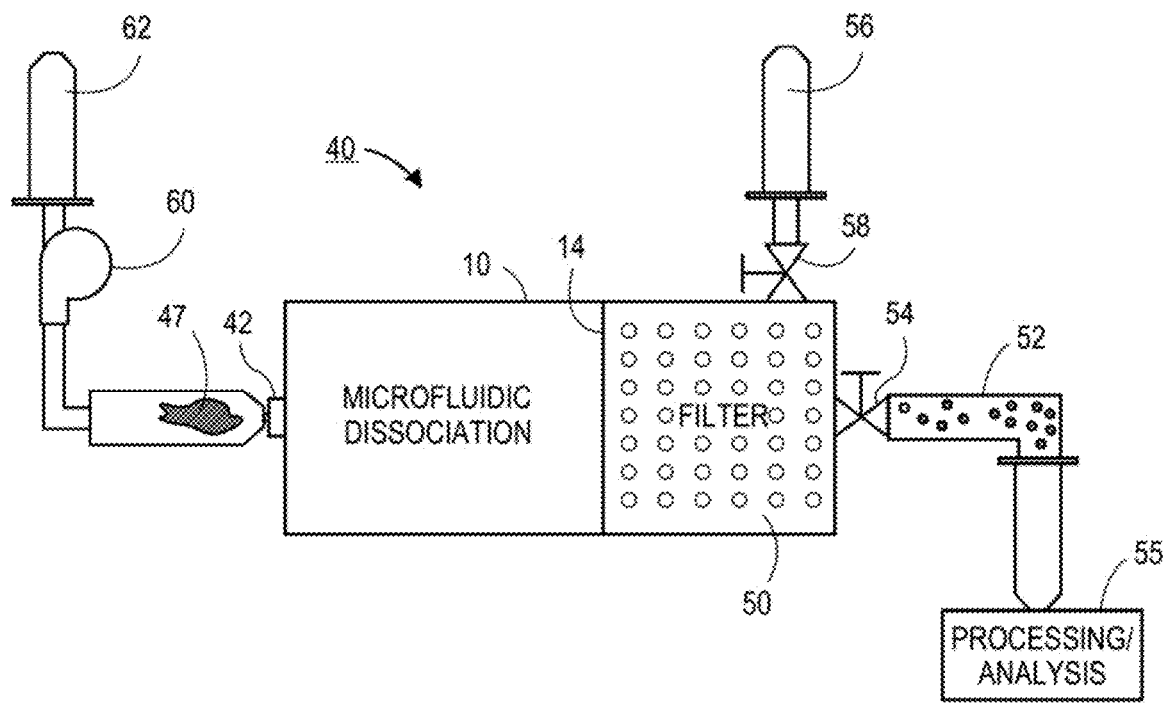
FIG. 8 illustrates a system integrating the tissue dissociation device according to another embodiment.

Referring now to FIGS. 6-8 are different embodiments of a system 40 that is used to dissociate tissue that incorporates the tissue dissociation device 10. FIG. 6 illustrates one embodiment of a system 40 that uses "off chip" pumping to flow fluid and tissue through the tissue dissociation device 10. A sample port 42 is illustrated that is connected or coupled to a syringe device 44. Sample port 42 could be in the inlet 12 or it could be another port that is used to transfer sample to and from the tissue dissociation device 10. The syringe device 44 may be coupled a syringe pump 46 or the like that is used to actuate the syringe device 44 to depress or withdrawal the syringe plunger 45 on an as needed basis. As seen in FIG. 6, the outlet 14 of the tissue dissociation device 10 is connected to an optional filter 50. The filter 50 is used to permit single cells to pass through the filter 50 while cell aggregates are retained in the tissue dissociation device 10. In one aspect, the filter 50 is a microfabricated porous membrane. A porous membrane that is directly fabricated by photolithography may be used, as this will improve pore uniformity and density and simplify production in comparison to alternative approaches that require multiple rounds of deposition, photolithography, and etching. Of course, it should be understood that other filters 50 besides the microfabricated porous membrane may be used.

The porous membrane may be created by using a photosensitive polymer (e.g., 1002F and SU-8) and thinner that are mixed in equal parts and deposited on a silicon wafer by spin coating. A photomask is then be aligned, UV exposed, and developed. This process may be used to create pores having a diameter within the range of 30-100 μm that fill 18% of the total surface area. The membranes are 4 μm thick and 6 mm in diameter, and are reinforced with paper. Additional details regarding the formation a microfabricated porous membrane may be found in Kim, M. Y. et al., Microfabrication of High-Resolution Porous Membranes for Cell Culture, J. Memb. Sci. 452, 460-469 (2014), which is incorporated by reference herein.

Single cells passing through the filter 50 then continue onward to an outlet 52. The outlet 52 also includes a valve 54 therein that is used, as described below, when additional passes of tissue sample (e.g., larger clusters of cells retained in the tissue dissociation device 10) are run through the device 10. The single cells in the outlet 52 may then move downstream for additional processing and/or analysis as illustrated in downstream process 55. For example, the cells may be focused (using, for example, inertial focusing), sorted, or labeled with probes. The cells may be analyzed downstream. For example, labeled cells can be identified or quantified. Cells may be subject to downstream deformability measurements, for example. Additional downstream processes include micro-NMR, ELISA, and flow cytometry.

As seen in FIG. 6, the system 40 includes a buffer solution 56 that is connected to the filter 50 via a valve 58. The valve 58 can be turned on/off as described below when a sample is run through the tissue dissociation device 10 in multiple passes. The buffer solution may include a buffer that is compatible with the cells passing through the device such as PBS buffer. Alternatively, the valves 54, 58 may be combined into a single valve such a three-way valve.

To operate the system 40, tissue samples are obtained. Tissue samples may be obtained, for example, using a biopsy procedure (e.g., needle biopsy). The tissue samples are loaded into a fluid solution 47 as seen in FIG. 6. The fluid solution may contain only a buffer such as PBS or the like. Alternatively, in other embodiments, a chelating agent like EDTA may be contained in the fluid to aid in dissociating single cells from larger bodies or clusters. In still other embodiments, proteolytic enzymes such as Trypsin or Collagenase may be included in the fluid solution. Digestion enzymes may also be included along with a chelating agent (e.g., EDTA). Generally, it is preferred to avoid the use of Trypsin because of its ability to cleave cell surface proteins that may provide important diagnostic information or regulate cell function.

The tissue dissociation device 10 may be washed with a buffer prior to introduction of the sample. For example, SuperBlock Blocking Buffer (Thermo Scientific) can be inserted into the tissue dissociation device 10 and allowed to incubate for fifteen (15) minutes at room temperature. The SuperBlock Blocking Buffer is a proprietary protein formulation in phosphate-buffered saline (pH 7.4) with Kathon preservative.

With the syringe 44 connected to the device 10, the syringe pump 46 is activated whereby sample is run through the tissue dissociation device 10. During operation of the syringe pump 46, the valve 54 to the outlet 52 is open while the valve 58 to the buffer solution 56 is closed. In this embodiment, single cells formed within the tissue dissociation device 10 pass through the filter 50 while larger clusters of cells are retained by the filter 50. In some embodiments, only a single pass through the tissue dissociation device 10 is sufficient to extract the needed amount of single cells. In other embodiments, however, multiple passes of the tissue through the device are needed to recover additional single cells. In a multi-pass mode, after the first pass of sample is performed through the tissue dissociation device 10, the valve 54 to the outlet 52 is closed and the valve 58 to the buffer solution 56 is opened. The syringe pump 46 then operates in reverse to withdraw the plunger 45 whereby buffer solution 56 is pulled into the tissue dissociation device 10. Approximately 1 mL of buffer solution 56 is pulled into the tissue dissociation device 10 which is around the total volume of the fluidic channels and vias in the tissue dissociation device 10. After buffer solution 56 has been pulled back into the tissue dissociation device 10, the valve 58 to the buffer solution 56 is then closed and the valve 54 to the outlet 52 is opened and the syringe 44 can then push sample back through the tissue dissociation device 10. This process can be repeated any number of times. It should be understood that the presence of the filter 50 is optional. In some embodiments, the filter 50 can be omitted entirely in which case the outlet 52 is coupled directly to the outlet 14 of the device 10. Moreover, the buffer solution 56 and the valve 58 can be coupled directly to the tissue dissociation device 10 instead of the filter 50.

FIG. 7 illustrates an alternative embodiment of the system 40 with similar features to those of the embodiment of FIG. 6 numbered similarly. In this embodiment, the filter 50 has been omitted. Moreover, there are no valves or buffer as was used in the prior embodiment. This embodiment may be used, for example, when a single pass is made through the tissue dissociation device 10. FIG. 8 illustrates another alternative embodiment of the system 40 with similar features numbered similarly. In this embodiment, rather than use an external pumping source like a syringe pump 46, an on-chip pump 60 is used to pump the tissue containing fluid 70 through the tissue dissociation device 10. The on-chip pump 60 may be coupled to a buffer 62 as illustrated in FIG. 8. A number of on-chip pumps 60 could be employed in this embodiment. For example, a pneumatic-based pumping system where pneumatic pumps and valves can be directly incorporated on-chip in the tissue dissociation device 10. Other on-chip pumps 60 may also be used such as, for example, peristaltic, rotary, mechanical, magneto-hydrodynamic, and the like.

In another alternative embodiment, rather than construct the tissue dissociation device 10 produce single cells, the device 10 may be constructed to produce clusters of cells of a defined size (e.g., clusters of cells having a size of 50, 75, or 100 μm). This is accomplished be removing one or more of the most downstream stages from the device 10. This would make the smallest channel dimension, for example, within the range of 250 to 500 μm rather than 125 μm. Alternatively, rather than omitting one or more downstream stages, the initial stage may be widened in dimensions (e.g., 4 to 8 mm rather than 2 mm) to generate clusters of cells. Clusters of cells are desired, for instance, for drug testing studies as they are more representative of actual tumors.

Experimental

A multi-layer device as illustrated in FIGS. 1, 3, 4, 5, and 7 was evaluated for the dissociation performance. Using multiple cultured tumor tissue models showed that the device significantly improves single cell recovery following enzymatic treatment because small clusters of cells can be dissociated more effectively. Superior results were also observed under enzyme-free conditions that better maintain molecular expression, and in all cases processing required less than ten minutes.

Figure 9:
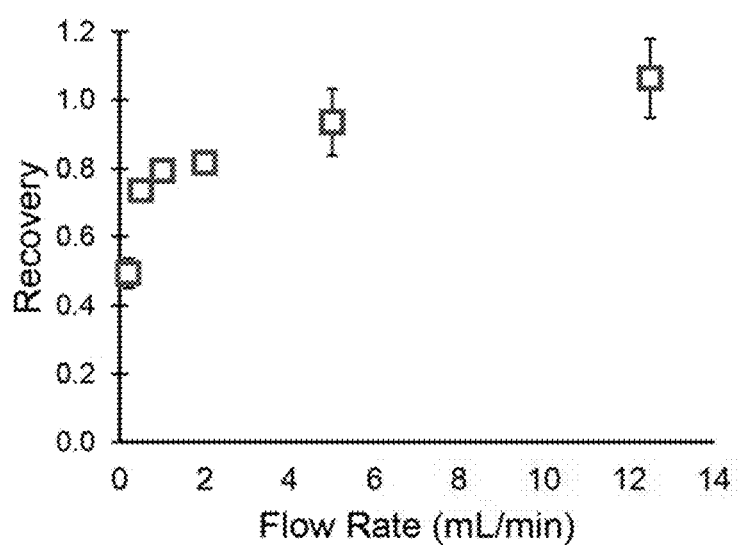
FIG. 9 illustrates a graph of HCT116 cancer cell recovery plotted as a function of flow rate. Samples were a cell suspension obtained by first treating with trypsin, then run at 12.5 mL/min flow rate for 1 pass. Sample concentration was fixed at $10^6$ cells/mL.
Figure 10A:
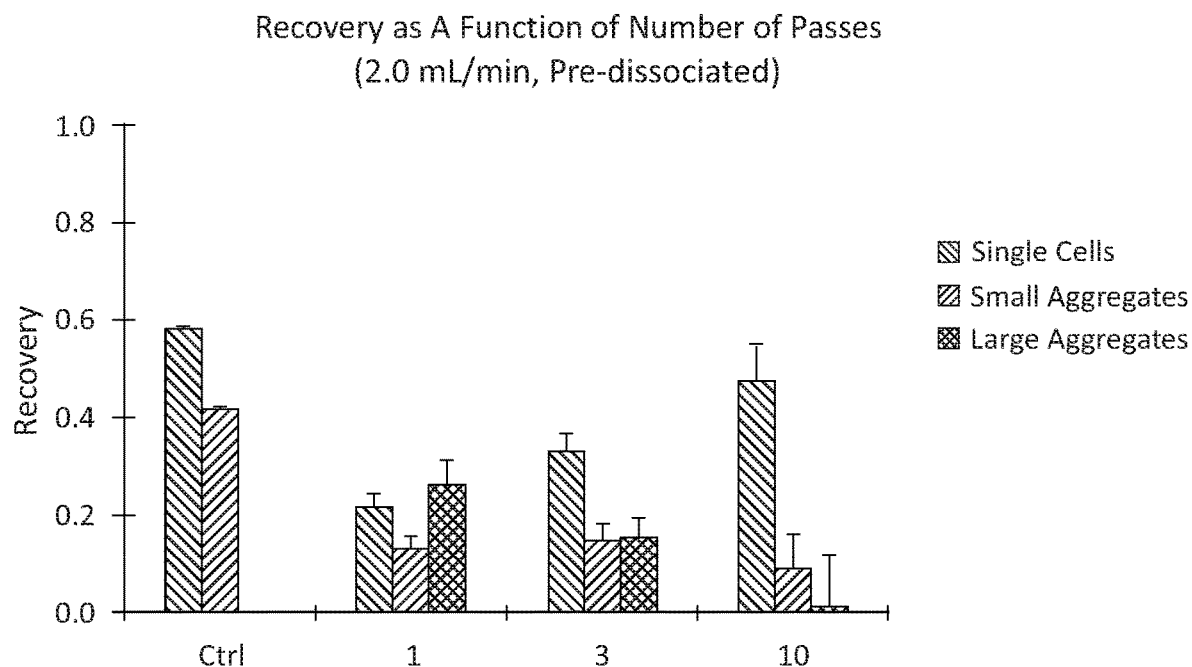
FIG. 10A illustrates cell recovery from HCT116 monolayer sheets recovery plotted as a function of number of passes with trypsin control included. Samples were run at 2.0 mL/min. Trypsin treated control populations are normalized to 1.
Figure 10B:
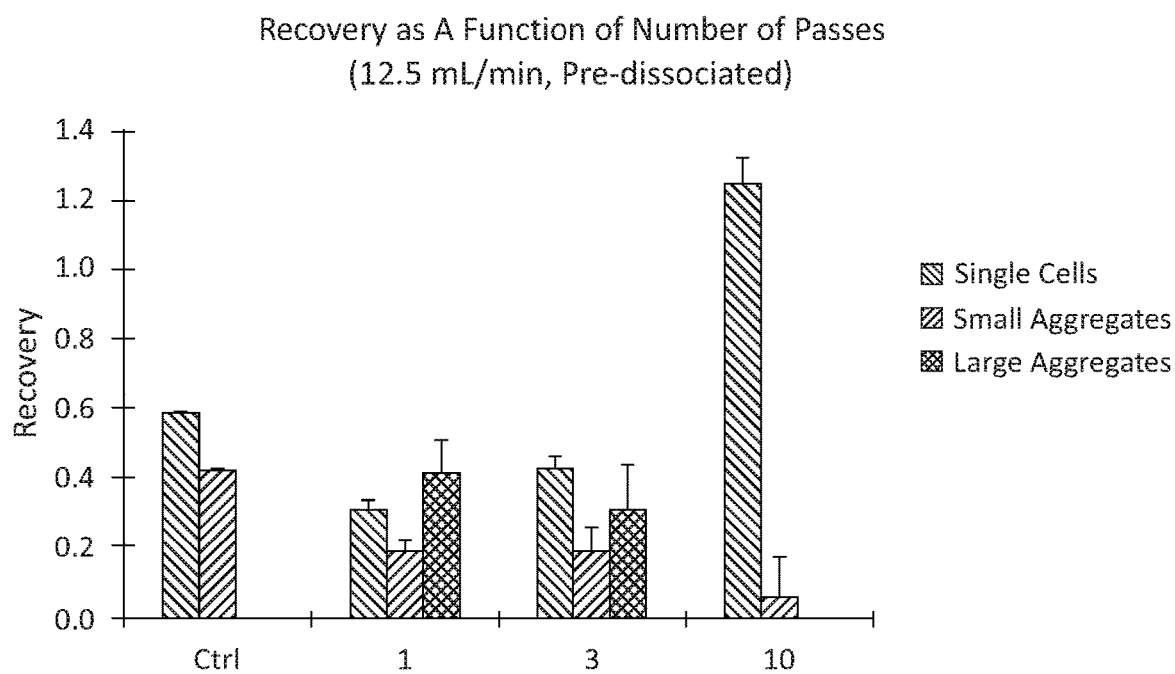
FIG. 10B illustrates cell recovery from intact HCT116 monolayer sheets plotted as a function of number of passes with trypsin treated control included. Samples were run at 12.5 mL/min. Trypsin control populations are normalized to 1.

Initially, a cell suspension was introduced into the device to determine whether sample may be lost due to hold up or damage induced by shearing. HCT 116 colon cancer monolayers were employed that were digested with trypsin-EDTA and mechanically sheared (pipetting and vortexing) per routine culture procedures. The cell suspensions were introduced into the device using a syringe pump and tested the effect of different flow rate and cell concentration conditions. Afterward the device was washed with buffer and cell recovery was assessed using a cell counter. It was found that sample recovery increased progressively over the range of flow rates tested, from approximately 50% at 0.2 mL/min up to almost 100% at 12.5 mL/min as seen in FIG. 9. In addition, a shift in the population to smaller sizes was also observed that scaled with flow rate. It is believed that the larger species correspond to small clusters of two (2) or more cells that remained together after trypsin treatment. FIGS. 10A and 10B illustrate the normalized recovery of cells obtained from intact monolayer sheets using only the device (for different numbers of passes). FIG. 10A shows samples run at a flow rate of 2.0 mL/min. FIG. 10B shows samples run at a flow rate of 12.5 mL/min. Single cells (9-17 μm) and small clusters (>17 μm) are defined from a cell count of the device effluent. Large aggregates are counted after the effluent is treated with trypsin.

This is a common result for routine cell culture, where additional treatment is not encouraged because it would decrease cell viability and the small clusters do not negatively affect results. The device was significantly more effective at dissociating these small cell clusters, resulting in a truer single cell suspension. Evidence for this conclusion can be found in the fact that the device yielded a cell population that was evenly distributed around an average diameter of 13-14 μm, which is consistent with microscopic analysis of HCT 116 cells. FIGS. 10A and 10B illustrate histogram data showing that the device produced a true single cell suspension after ten (10) passes through the device. Control samples had a similar peak size, but also a delayed decrease in the distribution at larger sizes. Thus, we could establish a single cell window around the 13.5 μm mean diameter, from 9.5 μm to 17.5 μm. For the data in FIG. 9, approximately 25% of the control sample was small clusters and this percentage decreased with flow rate down to only 6%. This further confirms the conclusion that the small clusters were dissociated rather than selectively retained in the device, as recovery at 12.5 mL/min flow rate could not otherwise approach 100%. Since recovery at this condition also did not significantly exceed 100%, significant cell losses must have been incurred to offset cluster dissociation. Cell losses at lower flow rates were likely due to non-specific sticking or entrapment in low flow regions (i.e., channel expansion or branch points).

While dissociating small cell clusters is promising, a primary goal is to process tumor tissues. As a starting point, a simple tissue model was created consisting of cell monolayers that were released as intact sheets. This was accomplished by growing HCT 116 cells to confluency on collagen and treating with collagenase. These tumor sheets contained approximately 100,000 cells that indeed remained connected to each other after suspension.

Dissociation experiments were conducted by passing a tumor sheet directly through the device in buffer, and afterwards the device effluent was collected and the single cell and small cluster cell yields were assessed with a cell counter as discussed above. To determine if large aggregates passed through the device, samples were then treated with trypsin-EDTA and sheared by pipetting and vortexing prior to a second cell count. Control sheets only received trypsin-EDTA, pipetting, and vortexing procedures. Using a flow rate of 2 mL/min, it was found that in a single device pass only one-third of the sample was recovered as single cells and small clusters. Counting large aggregate only increased total recovery to 60%, suggesting that significant sample remained within the device. An investigation was performed on whether passing the sample through the device multiple times could improve results. This was achieved by reversing flow to reposition the sample prior to the next run. It was found that single cell and small cluster yields improved up to 60% after 10 passes, but total yield remained the same. The percentage of single cells to small clusters did improve however, from 60% for the trypsin control to 80% after the device. Increasing flow rate to 12.5 mL/min improved results dramatically as seen in FIG. 10B. Single cell and small cluster yield improved with pass number from around half of the trypsin control value to 1.5-fold greater. Cell yield was able to exceed the trypsin control because small cell clusters now accounted for only 4% of the sample after 10 passes, reflecting significantly more efficient liberation of single cells. Total yield was near or exceeded the trypsin control, suggesting that sample was not lost within the device at the high flow rate condition.

Figure 11A:
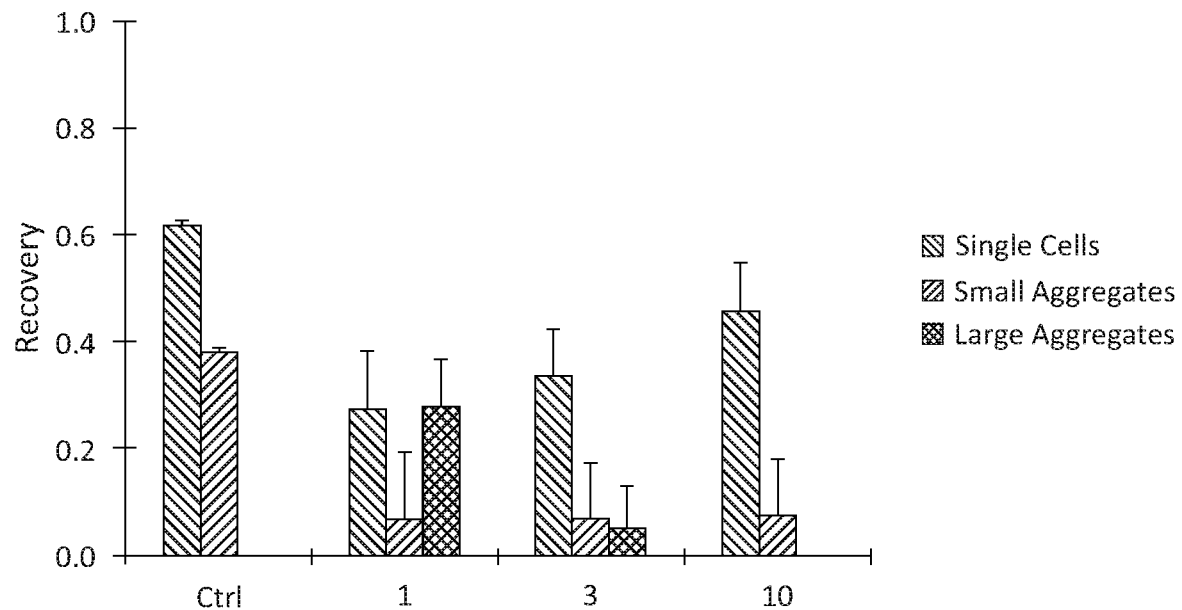
FIG. 11A illustrates cell recovery from HCT116 spheroids plotted as a function of number of passes with trypsin control included. Samples were run at 12.5 mL/min.
Figure 11B:
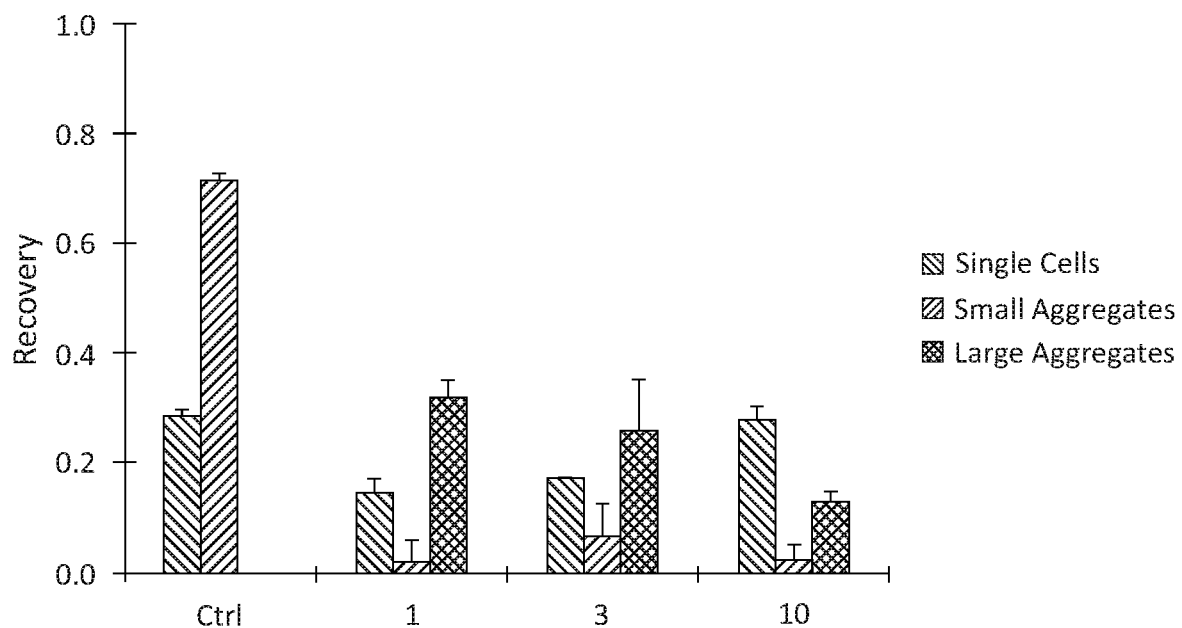
FIG. 11B illustrates cell recovery form NCI-H1650 spheroids plotted as a function of number of passes with trypsin control included. Samples were run at 12.5 mL/min.
Figure 11C:
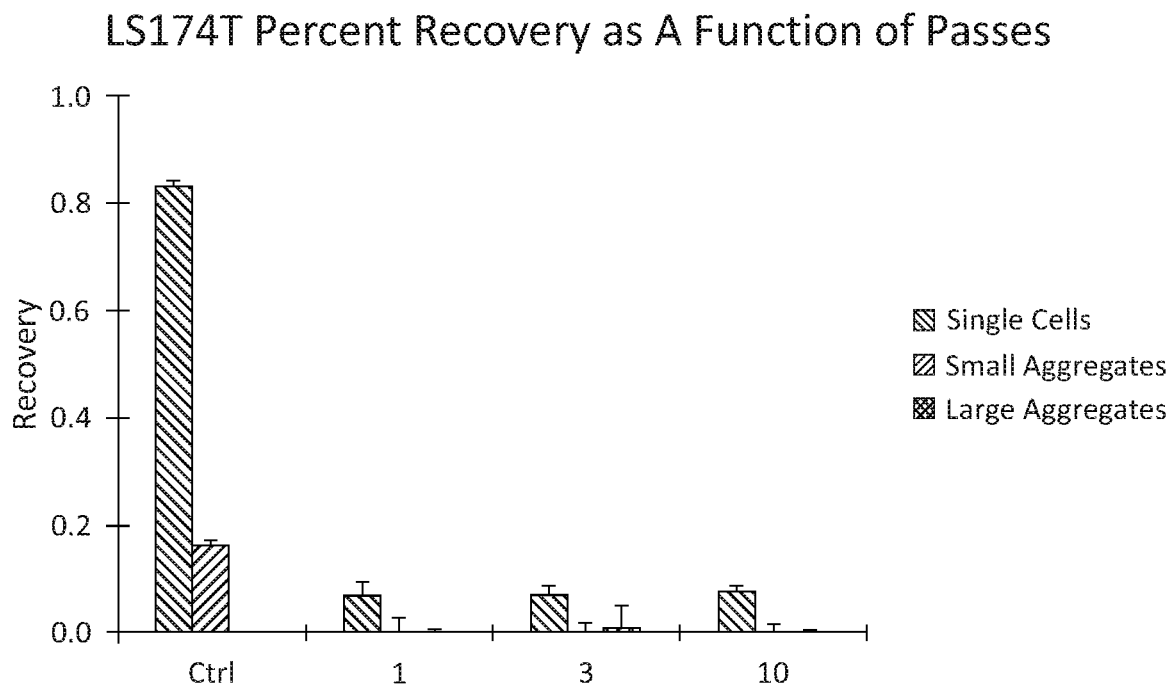
FIG. 11C illustrates cell recovery from LS 174T spheroids plotted as a function of number of passes with trypsin control included. Samples were run at 12.5 mL/min.

Next tumor spheroids were employed, which are a more advanced model with three-dimensional structure that better represents solid tumors. Spheroids were prepared via the hanging drop method and were collected after reaching 250-300 μm diameter. HCT 116 cells were used as already discussed, as well as NCI-H1650 lung and LS 174T colon cancer cells. In each case the spheroids contained approximately several hundred cells. Dissociation experiments were conducted after pooling multiple spheroids into a single sample and procedures were identical to the tumor sheet studies above. Results obtained for 12 pooled HCT 116 spheroids that were processed at 12.5 mL/min flow rate for different number of device passes are illustrated in FIGS. 11A-11C. Overall, recovery was similar to HCT 116 tumor sheets processed at 2 mL/min flow rate. Single cell recovery was low after a single pass, and increased with additional treatment up to approximately ½ of the trypsin control. A significant population of small clusters was present for each condition, all at approximately 10%. Total cell yield was 60% after 1 pass, but actually decreased slightly with additional treatment, possibly indicating cell damage. Similar results were observed for NCI-H1650 (FIG. 11B) and LS 174T (FIG. 11C) spheroids, but with progressively lower yields in each case. This is presumably because these cells are more cohesive, as they do require longer digestion times with trypsin. Finally, 10 pass experiments were performed with different numbers of HCT116 spheroids, and found recovery results that scaled directly with sample size. Remarkably, results were consistent down to only a single spheroid.

Figure 12A:
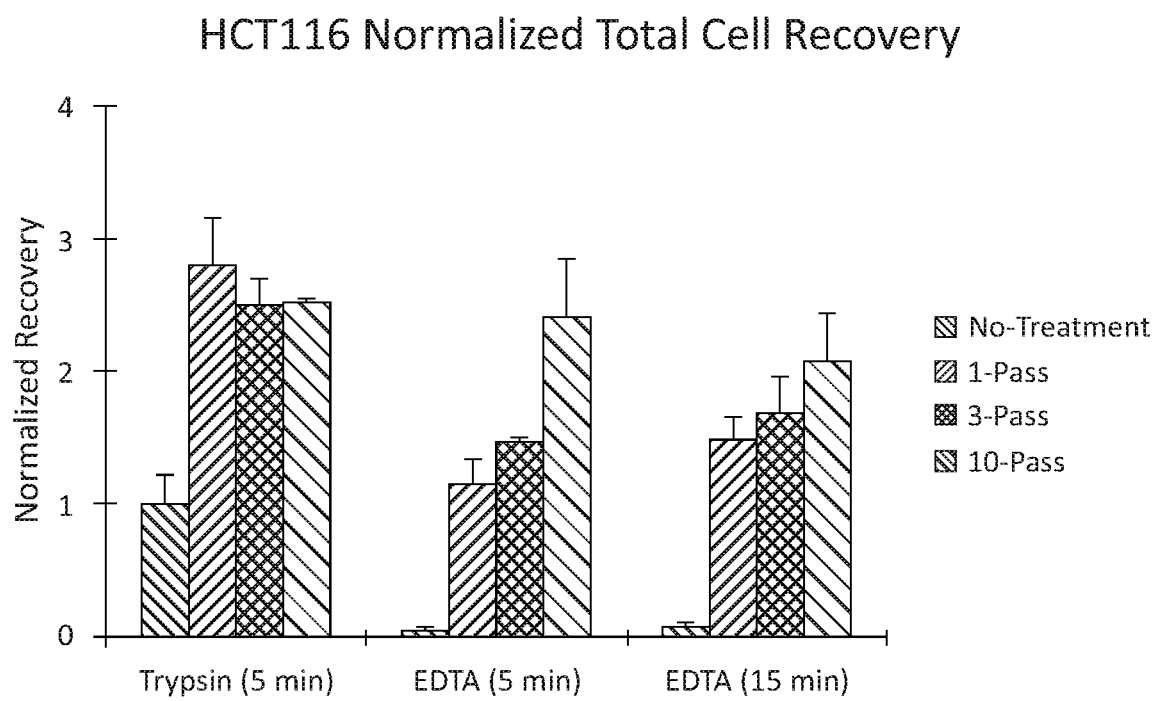
FIG. 12A illustrates cell recovery from HCT116 spheroids following various treatment conditions (trypsin alone for 5 minutes, EDTA alone for 5 minutes, and EDTA alone for 15 minutes). Samples were run at 12.5 mL/min for various numbers of passes (1, 3, and 10). Controls were not passed through the device.
Figure 12B:
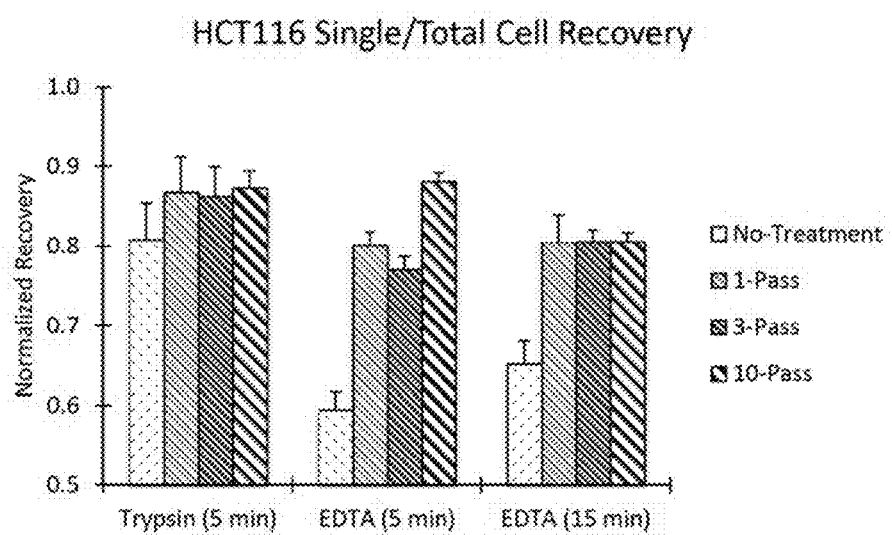
FIG. 12B illustrates single cell recovery from HCT116 spheroids following various treatment conditions (trypsin alone for 5 minutes, EDTA alone for 5 minutes, and EDTA alone for 15 minutes).
Figure 12C:
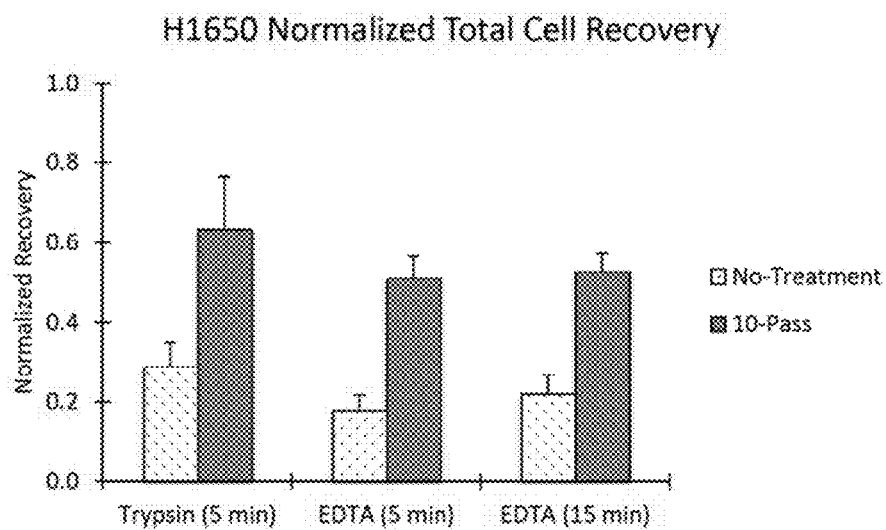
FIG. 12C illustrates cell recovery from NCI-H1650 spheroids following various treatment conditions (trypsin alone for 5 minutes, EDTA alone for 5 minutes, and EDTA alone for 15 minutes). Samples were run at 12.5 mL/min for various numbers of passes (1, 3, and 10). Controls were not passed through the device.
Figure 12D:
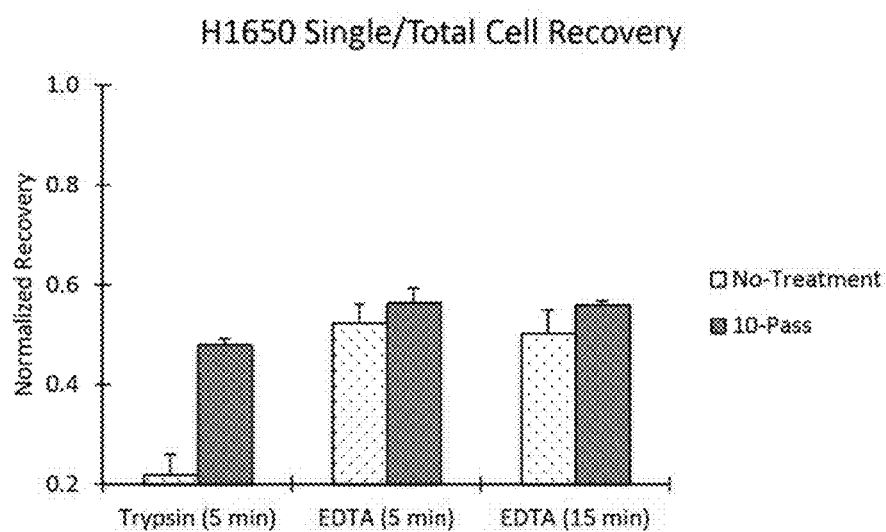
FIG. 12D illustrates single cell recovery from H1650 spheroids following various treatment conditions (trypsin alone for 5 minutes, EDTA alone for 5 minutes, and EDTA alone for 15 minutes).
Figure 12E:
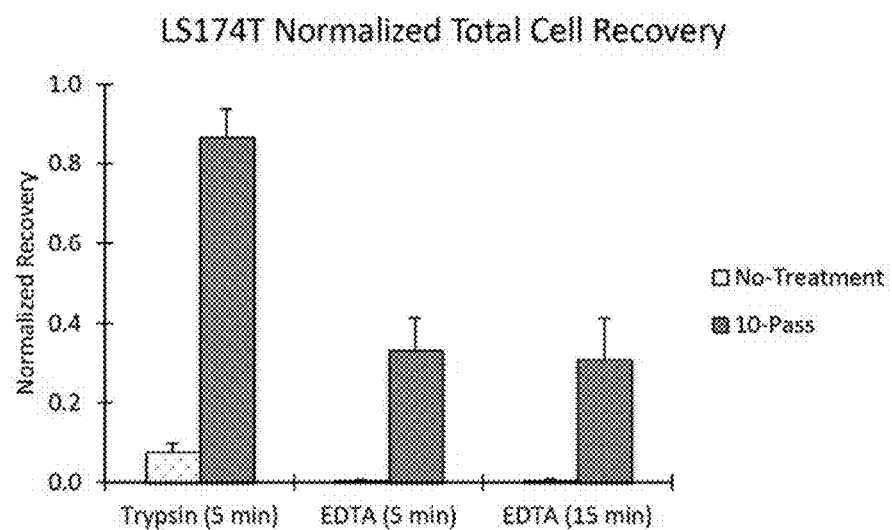
FIG. 12E illustrates cell recovery from LS 174T spheroids following various treatment conditions (trypsin alone for 5 minutes, EDTA alone for 5 minutes, and EDTA alone for 15 minutes). Samples were run at 12.5 mL/min for various numbers of passes (1, 3, and 10). Controls were not passed through the device.
Figure 12F:
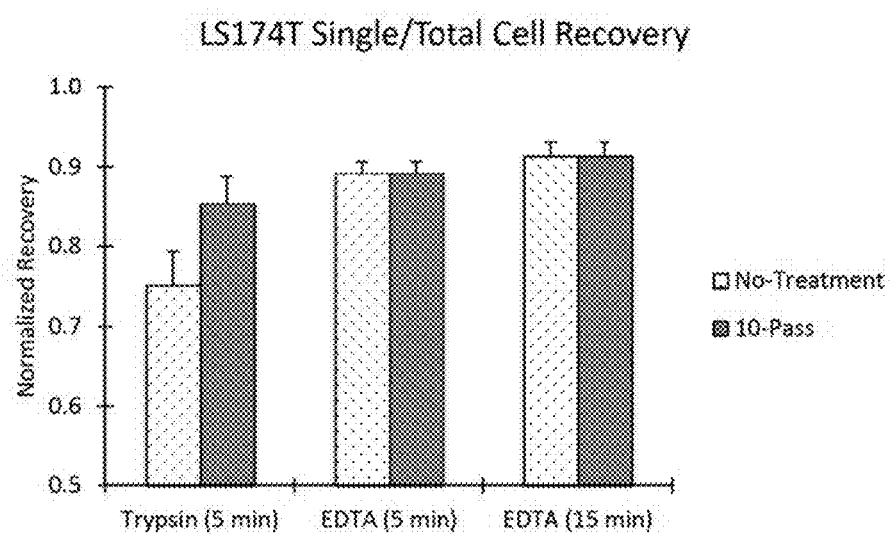
FIG. 12F illustrates single cell recovery from LS 174T spheroids following various treatment conditions (trypsin alone for 5 minutes, EDTA alone for 5 minutes, and EDTA alone for 15 minutes).

Although dissociation of tumor spheroids exclusively using hydrodynamic forces was inefficient, this would be an unnecessarily stringent goal for practical purposes. Tumor tissues are currently treated with proteolytic enzymes prior to mechanical procedures. Therefore device performance was tested after brief exposure to trypsin-EDTA. Also tested was brief exposure to EDTA treatment alone. After digestion of HCT116 spheroids for 5 minutes, cell yield improved 3-fold after a single pass as seen in FIG. 12A. Single cell percentage also rose from 80% for the control to 85% for the device as seen in FIG. 12B. Additional passes did not improve results as single cell yield was already very high. Treatment of HCT 116 spheroids with EDTA for 5 min was extremely inefficient, but the device increased recovery dramatically. Compared to the trypsin control, yield was similar following a single pass and increased 2.5-fold after further device processing. Increasing EDTA exposure time enhanced recovery for all but the 10 pass case. Similar results were observed for NCI-H1650 and LS 174T spheroid cases as seen in FIGS. 12C, 12D (H1650 spheroids) and FIGS. 12E and 12F (LS 174T spheroids).

Figure 13A:
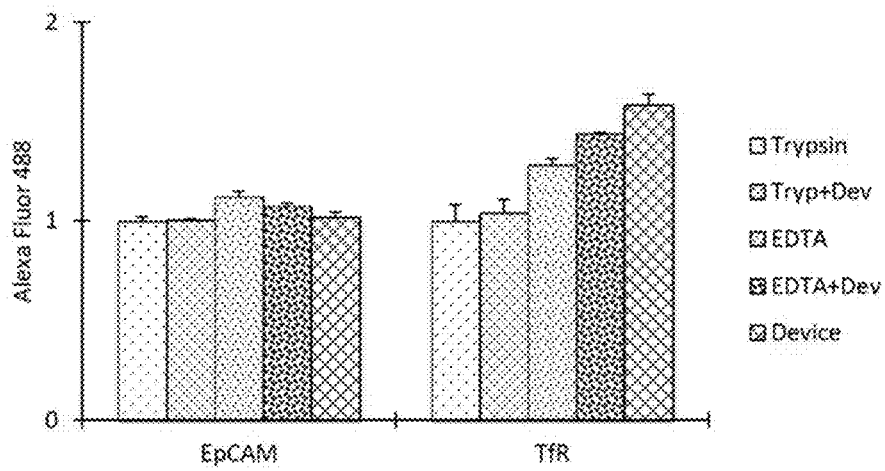
FIG. 13A illustrates cancer biomarker expression cells recovered from spheroids after various treatments, including trypsin, EDTA, or the device alone or combinations of trypsin or EDTA followed by the device. TfR is sensitive to trypsin, resulting in lower expression levels when it was used.
Figure 13B:
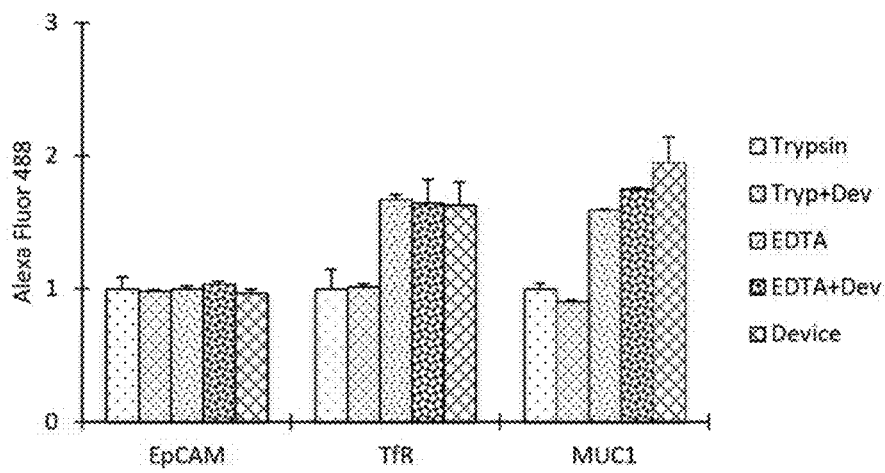
FIG. 13B illustrates cancer biomarker expression of NCI-H1650 spheroids after various treatments, including trypsin, EDTA, or the device alone or combinations of trypsin or EDTA followed by the device. TfR and MUC1 are sensitive to trypsin, resulting in lower expression levels when it was used.

Diagnostic and cell sorting applications require specific biomarkers to provide information or select for unique cell subpopulations. Surface proteins are typically employed because they are easier to access for live cells, but this also increases the likelihood that these protein targets are damaged. To illustrate the potential impact of the different dissociation procedures used in the previous section, surface protein expression was measured by flow cytometry on cell suspensions following treatment. Epithelial cell adhesion molecule (EpCAM), transferrin receptor (TfR), and mucin 1 (MUC1) were selected for this study because they are surface proteins and common cancer biomarkers. Furthermore, TfR and MUC1 are cleaved by trypsin, leading to lower expression levels. EpCAM is not sensitive to trypsin, but is a homotypic cell-cell junction protein that could be affected by mechanical separation. It was found that EpCAM expression for HCT 116 and NCI-H1650 spheroids was similar for all dissociation treatments as seen in FIGS. 13A and 13B. Brief exposure to trypsin did lower expression of TfR and MUC1 relative to EDTA treatment, by approximately 25 to 50%. Differences were more pronounced for longer trypsin digestion times. Device treatment at 12.5 mL/min flow rate for 10 passes did not significantly alter trypsin or EDTA results. Slightly elevated expression of TfR and MUC1 was observed when the device was used alone. This result may be related to cell damage inflicted by hydrodynamic forces, as some loss of cell membrane integrity could lead to labeling of intracellular stores of the target, or simply small sample size biasing since cell recovery is much lower. Note that MUC1 was not measured for HCT 116 cells because expression is very low. LS 174T cells do not express significant TfR or MUC1, but similar results were observed for EpCAM. These findings demonstrate the potential power of non-enzymatic dissociation methods such as the device, working alone or in concert with EDTA, for preserving surface biomarker expression.

While embodiments of the present invention have been shown and described, various modifications may be made without departing from the scope of the present invention. The invention, therefore, should not be limited, except to the following claims, and their equivalents.

What is claimed is:

1. A method of dissociating tissue comprising:
obtaining a sample of tissue from a subject;
pumping the sample of tissue into a tissue dissociation device comprising an inlet, a plurality of serially arranged stages of channels, each channel defined by a continuous expansion and constriction of the channel width, wherein the plurality of serially arranged stages each split into a multiple channels having a decreased channel width as compared to the channel width of a preceding stage with each serially arranged stage of decreased width generating jets of fluid with increasing dissociation power, and an outlet; and
collecting the processed sample from the outlet after pumping the tissue sample through the plurality of serially arranged stages of channels, wherein the processed sample contains dissociated tissue that comprises clusters of cells or single cells.

2. The method of claim 1, wherein the sample of tissue is pumped through the plurality of serially arranged stages of channels in multiple passes.

3. The method of claim 2 wherein the multiple passes comprises pumping the sample of tissue through the plurality of serially arranged stages of channels in a first direction followed by pumping the sample of tissue through the plurality of serially arranged stages of channels in a second, opposing direction.

4. The method of claim 2 wherein a syringe pump is used to pump the sample of tissue in multiple passes through the plurality of serially arranged stages of channels in repeated forward and reverse directions.

5. The method of claim 4, wherein when pumping in the reverse direction, a buffer solution fluidically connected to the tissue dissociation device via a valve is pulled through the tissue dissociation device by the syringe pump.

6. The method of claim 5, wherein a filter is connected to the outlet, wherein the filter allows the passage of single cells while retaining cell aggregates.

7. The method of claim 1, wherein the sample of tissue is pumped using an external pump.

8. The method of claim 1, wherein each of the plurality of stages are located in different layers of the tissue dissociation device.

9. The method of claim 1, wherein the tissue is treated with a proteolytic enzyme prior to or during pumping the sample into the tissue dissociation device.

10. The method of claim 1, wherein the processed sample is filtered prior to collection.

11. The method of claim 1, wherein the tissue comprises tumor tissue.

* * * * *